(12) United States Patent
Honda et al.

(10) Patent No.: US 6,592,858 B1
(45) Date of Patent: Jul. 15, 2003

(54) FIBER STRUCTURE HAVING DEODORIZING OR ANTIBACTERIAL PROPERTY

(75) Inventors: Hidenobu Honda, Shiga (JP); Naoaki Ito, Shiga (JP); Hiroe Yokoi, Kyoto (JP); Masaki Ishii, Shiga (JP); Koichi Saito, Shiga (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/937,423

(22) PCT Filed: Jan. 26, 2000

(86) PCT No.: PCT/JP00/00371

§ 371 (c)(1),
(2), (4) Date: Sep. 26, 2001

(87) PCT Pub. No.: WO01/55498

PCT Pub. Date: Aug. 2, 2001

(51) Int. Cl.[7] .......................... A61L 9/00; A01N 25/34; B32B 3/02; B32B 19/00
(52) U.S. Cl. ..................... 424/76.1; 424/402; 428/357; 428/96
(58) Field of Search ............................. 424/76.1, 402; 428/357, 96

(56) References Cited

FOREIGN PATENT DOCUMENTS

| EP | 0728855 | * | 2/1996 |
|----|---------|---|--------|
| EP | 0 712 662 A2 | | 5/1996 |
| EP | 0 728 855 A1 | | 8/1996 |
| EP | 1 045 065 | | 10/2000 |
| JP | 4-174781 | | 6/1992 |
| JP | 5-55184 | | 8/1993 |
| JP | 8-74171 | | 3/1996 |
| JP | 9-84860 | | 3/1997 |
| JP | 10-1879 | | 1/1998 |
| JP | 10001879 | * | 1/1998 |
| JP | 10 292267 | | 11/1998 |
| JP | 10-292268 | | 11/1998 |
| JP | 10292268 | * | 11/1998 |
| JP | 11 323726 | | 11/1999 |
| JP | 2000 110064 | | 4/2000 |
| JP | 2000 192368 | | 7/2000 |

* cited by examiner

Primary Examiner—Jose G. Dees
(74) Attorney, Agent, or Firm—Piper Rudnick LLP

(57) ABSTRACT

This application relates to a fibre structure which has, on the fibre surface, a complex oxide comprising titanium and silicon, plus a binder. In particular, it relates to a fibre structure which preferably has, on the fibre structure, a complex oxide comprising titanium and silicon, and at least one type of binder selected from alkyl silicate resins, other silicone resins and fluororesins, and it provides a fibre structure having durable deodorant properties, antibacterial properties, antifungal properties or antisoiling properties.

14 Claims, 1 Drawing Sheet

FIBER STRUCTURE HAVING DEODORIZING OR ANTIBACTERIAL PROPERTY

TECHNICAL FIELD

The present invention relates to a fibre structure with outstanding deodorant properties, residual-odour prevention properties, antibacterial properties and/or antifungal properties, etc, of durability not found hitherto. Such a fibre structure can be applied widely to, for example, clothing, curtains, wall covering materials, sheet materials, bedding and other such interior materials, and the interior trim materials of automobiles and other vehicles.

BACKGROUND ART

In recent years, along with improvements in standards of living, awareness of health and hygiene has also increased and, in the fields of clothing, food and housing, practical use is being made of products and techniques where deodorant, antibacterial, antifungal and antisoiling processing is employed. In particular, in the field of clothing, various deodorant, antibacterial and antifungal processing techniques have been developed. Furthermore, developments have also progressed in other areas such as household interiors.

For example, photocatalysts employed immobilized on the surface of an inorganic material such as a ceramic or glass are effective in terms of their deodorant properties, antibacterial properties, antifungal properties and antisoiling properties but, in order to fix photocatalysts to fibres, acrylic or urethane binders have hitherto been used and, since these are organic materials, the binders are themselves decomposed by the powerful oxidative decomposition capacity of the photocatalysts, causing problems such as discoloration and bad odours.

Other types of deodorant chiefly comprise those based on a neutralizing action, and few of these can exhibit a sustained deodorant function. For example, although acidic titanium oxide, aluminium sulphate and the like do show an effect in terms of deodorizing ammonia and other alkaline malodours, they are ineffective against bad smells which are neutral. Furthermore, in the case of zinc oxide where the deodorant itself is a base material, while this will neutralize acidic malodours such methyl mercaptan and hydrogen sulphide and convert them into odourless materials, it is ineffective against neutral malodours. Moreover, in these deodorizing methods based on a neutralizing action, no further effect is exhibited once the deodorant becomes saturated, and so a treatment of some kind, such as washing, is required to restore function.

There are also known deodorants which utilise physical adsorption, such as active carbon and silica. However, with these, the malodorous components are adsorbed and not decomposed, so they do not fundamentally resolve the situation. Ideally, it is necessary that malodorous components be completely decomposed to odourless components, but only a very few chemical materials are known which have such an action. For example, there is iron-phthalocyanine, and this material, which carries out oxidative degradation, has been incorporated into rayon fibre and used for example as a futon filler, and it has been confirmed that the odour of ammonia is thereby eliminated. Moreover, it is also known that hydrogen sulphide is oxidized to sulphur, mercaptans to disulphides, aldehydes to carboxylic acids and amines to ketones and ammonia. However, amongst these degradation products are some which themselves have a bad odour, and furthermore it cannot be said that chemical materials of this kind are effective against all bad odours. Specifically, they are not effective in eliminating the smell of tobacco or of perspiration.

Complex malodours like tobacco combustion gas are said to contain thousands of components, and deodorizing all of these has been difficult. Moreover, there are no deodorants which are effective against isovaleric acid, which is the principal component of human sweat. Again, the malodorous components of underarm odour are a mixture of several kinds of lower fatty acids and it has been difficult to render these completely odourless.

In the case of fibre structures which have been subjected to such deodorant processing, the adsorbed components may themselves give rise to a bad smell or the malodorous components may be changed by decomposition into other components which themselves produce a strange smell. In view of the problems of the prior-art, the present invention aims to offer a fibre structure with the outstanding functions of providing sustained deodorant, antibacterial, antifungal and antisoiling properties, without discoloration or degradation at the time of use.

DISCLOSURE OF INVENTION

In order to realise this objective, the present invention adopts the following means.

Specifically, the fibre structure of the present invention is characterized in that it has, on the fibre surface, a complex oxide comprising titanium and silicon, plus a binder. In particular, the invention relates to a fibre structure with outstanding deodorant, antibacterial and other properties which preferably has, on the fibre surface, a complex oxide comprising titanium and silicon, plus at least one type of binder selected from alkyl silicate resins, other silicone resins and fluororesins.

BEST MODE FOR CARRYING OUT THE INVENTION

Figure 1:
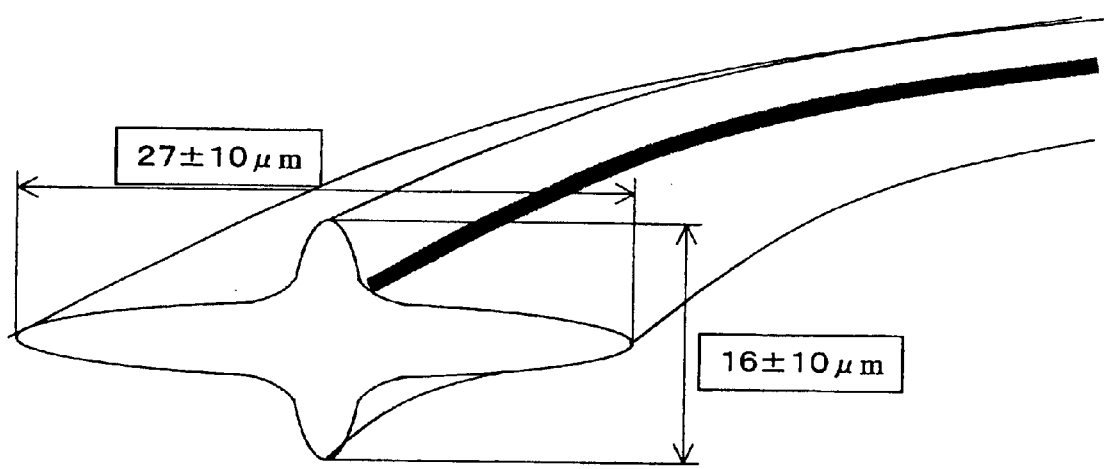
FIG. 1 shows the cross-sectional shape of fibre employed in Example 9.

In the present invention, photocatalyst refers to a substance with the property of being excited by ultraviolet light and oxidatively-degrading organic materials by means of its powerful oxidative capacity, and specific examples include those with a crystal structure referred to as being of the anatase type or rutile type.

In the present invention, attention has been directed to the fact that such a photocatalyst possesses deodorant properties, discolouring-material degrading and elimination properties (antisoiling properties) and disinfection properties (antibacterial and antifungal properties), and these may be manifested by conferral onto fibre structures.

For example, numerous processing techniques with a deodorizing function have been suggested hitherto but, in the case of these prior-art deodorizing techniques, there has been the problem that only specific odours are eliminated while the rest remain, and furthermore their durability and persistence has been poor.

However, with the photocatalyst of the present invention there may be achieved extremely outstanding effects not seen hitherto, in that there is shown a well-balanced deodorization of odours which have caused difficulties in the past, such as tobacco and body odours like perspiration odours, and furthermore, since the photocatalyst has the function of oxidatively degrading such odours, it prevents unpleasant residual/clinging odours. In addition, since it has the function of degrading and eliminating discolouring materials such as nicotine, it is also possible to achieve an antisoiling effect in respect of discolouring materials. Moreover, since the photocatalyst of the present invention has, on account of its oxidizing capability, a germicidal capacity in terms of, for example, methicillin-resistant *Staphyloccus aureus* (MRSA), *Escherichia coli* and *Staphyloccus aureus*, it is also possible to achieve antimicrobial and antifungal processing effects.

If the particle diameter of the photocatalyst is too great or if its specific surface area is too small, there is a tendency for the degradation rate of organic materials, in particular the degradation rate of bacteria, to decrease. Furthermore, it is thought that the deodorant reaction involves a process in which the malodorous components are adsorbed onto the catalyst and are then subjected to ultraviolet oxidative degradation, and since the ease or difficulty of malodorous component adsorption is thought to greatly influence the deodorant efficiency, the use of particles of primary particle diameter no more than 20 nm and having a specific surface area of 100–300 m$^2$/g is preferred. If the amount of photocatalyst affixed to the fibre structure is too low, the rate of decomposition of organic materials such as the malodorous components will be reduced, and satisfactory performance is not obtained. If the amount is too high, degradation of the fibre fabric is brought about due to the photocatalyst and the fabric handle also becomes harsh, so the fibre material becomes impractical and, furthermore, the bad smell generated as a result of oxidative degradation of the fibre or the binder, etc, by the photocatalyst itself becomes a problem. Hence, the amount of photocatalyst affixed to the fibre structure is preferably 0.03 to 10 wt % and more preferably 0.05 to 5 wt %, with the range 0.08 to 3 wt % being still further preferred.

It is important that there be used a complex oxide of titanium and silicon as the photocatalyst in the present invention. As said complex oxide, there may be used the catalyst produced by the method described in JP-B-5-55184. Generally speaking, binary complex oxides comprising titanium and silicon are known as solid acids, as described by, for example, K. Tanabe (*Shokubai* {*Catalysts*}, Vol.17, No.3, page 72 1975), and they exhibit marked acidity not observed in the respective oxides from which they are composed. Moreover, they have a high surface area. In other words, the complex oxides of titanium and silicon are not simple mixtures of titanium oxide and silicon oxide, but are recognized as exhibiting characteristic properties due to the fact that the titanium and silicon form a so-called binary oxide. Furthermore, the results of X-ray diffraction analysis have shown that this composite oxide has a non-crystalline or essentially non-crystalline microstructure. With regard to the proportions of the titanium and silicon by conversion to the oxide, preferred results are shown when the titanium oxide lies in the range 20–95 mol % and the silicon oxide lies in the range 5–80 mol %.I If the proportion of the silicon oxide is too great, there is a tendency for the photocatalytic activity capacity of the titanium oxide to be weakened, and so the optimum proportions should be determined according to the usage objectives. In a preferred method for the production of the complex oxide of titanium and silicon, titanium tetrachloride is mixed with a silica sol, then aqueous ammonia added dropwise, to produce a precipitate, and this precipitate is filtered off, washed and dried, after which it is calcined at 300–650° C. When compared to the generally-known titanium oxide photocatalysts, this catalyst is characterized in that its organic material oxidative degradation characteristics are not excessively strong, its antibacterial, deodorant, residual-odour-prevention and antisoiling properties are excellent as described above and, furthermore, the reduction in effect, the generation of a bad smell and discoloration, etc, which accompany decomposition of the binder are all suppressed.

It is especially preferred that the photocatalysts be applied onto the fibre surface along with at least one type of binder selected from alkyl silicate resins, other silicone resins and fluororesins. The complex oxide of titanium a silicon brings about decomposition of organic materials by irradiation of ultraviolet light, and it may bring about degradative discoloration of the fibre structure and binder resin, etc, so if for example a urethane resin or acrylic resin is present along with the photocatalyst, and ultraviolet irradiation takes place, there is discoloration or generation of a bad smell due to decomposition of this organic material.

In the present invention, by using at least one type of binder selected from alkyl silicate resins, other silicone resins and fluororesins for the purposes of affixing the photocatalyst comprising a complex oxide of titanium and silicon to the fibre structure, it is possible to prevent the decomposition, discoloration or generation of a smell characteristic of organic resin oxidation by the photocatalyst. Furthermore, in order to protect the fibre from decomposition due to oxidation by the photocatalyst, there may be provided an intermediate layer of an inorganic material such as titanium peroxide between the fibre and the binder containing the photocatalyst.

The alkyl silicates employed in the present invention are characterized in that they comprise primarily Si—O bonding regions and linear or branched saturated alkyls, and they have OH groups at the two ends. They include structures of the following kind.

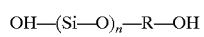

OH—(Si—O)$_n$—R—OH

In the formula, R is a linear or branched saturated alkyl group with 1 to 10 carbons, and n is an integer of value at least 1 and preferably a value in the range 1,000 to 10,000 in order to raise the inorganic character.

The alkyl group is a linear or branched saturated alkyl such as methyl, ethyl, propyl or isopropyl. There may be used a single such alkyl silicate or a mixture of two or more types may be employed. A characteristic feature of these compounds is that they readily undergo a dehydration reaction in the presence of heat, to form a polysiloxane coating. Alkyl silicates are water soluble and, following immersion of the fibre structure in a solution thereof, the fibre structure may be mangled and then treated at no more than 200° C. to produce a thin coating on the fibre surface.

It is also possible to directly affix the alkyl silicate to the surface of the fibre structure.

The photocatalyst may also be affixed by the mixing of a binder comprising a silicone resin or fluororesin. As stated above, these binders are excellent in their heat resistance, light resistance and chemical resistance, and they possess outstanding durability in terms of the oxidative capacity of the photocatalyst.

As the other silicone resins, there can be used crosslinking type resins belonging to the categories known as silicone resins or silicone varnishes, and said resins include those which can be obtained by condensation of a single crosslinking type resin like tetraethoxysilane or methyltrimethoxysilane, or a mixture of a number thereof. These form a resin of three-dimensional structure and, from amongst the silicone resins, they are the most outstanding in their heat and chemical resistance. Furthermore, there is the feature that, if the silicon oxide sol obtained by subjecting tetraisopropoxysilane or tetraethoxysilane to hydrolysis by means of strong acid in an alcohol/water mixed solvent is then dried, a glassy coating is formed. The structure obtained by such a sol/gel method is close to being inorganic, and is a further preferred structure in the present invention.

As fluororesins, the fluoroolefin polymers and the copolymers of fluoroolefins and vinyl ethers and/or vinyl esters have excellent properties, and so these are preferably employed. For example, polyvinyl fluoride, polytetrafluoroethylene, tetrafluoroethylene/perfluoroalkyl vinyl ester copolymers and vinyl ester/fluoroolefin copolymers show little decomposition and degradation, and are preferably used.

Unlike the normally-employed organic resins such as acrylic resins, urethane resins and epoxy resins, these silicone resins and fluororesins for the most part do not contain the hydrocarbon groups which are readily decomposed by the action of heat or chemicals. The silicone resins are composed primarily of Si—O bonds and the fluororesins are composed primarily of F—C bonds, and they contain just a small amount of hydrocarbon groups in the form of methyl groups or phenyl groups at the chain terminals or in side chains.

As a method for conferring water-absorption properties on this binder, or on the entire fibre structure containing photocatalyst on which said binder has been applied, there can be adopted the method of mixing with the binder, or applying to the fabric as a whole, a water-absorbing silicone resin with at least one type of group selected from hydrophilic hydroxyl groups (—OH), carboxyl groups (—COOH), amino groups (—NH$_2$) and amido groups (—CONH$_2$) or a water-absorbing silicone resin with a plurality of ethylene glycols, or a hydrophilicizing processing agent such as a compound containing polyethylene oxide groups or a cellulose, compound. Amongst the latter type of hydrophilicizing processing agents, it is preferred that there be used a hydrophilic polyester resin in which the chief component is a polyalkylene glycol/polyester block copolymer. Furthermore, the water-absorbing silicone resins of the former category may themselves be used as binders.

By employing such hydrophilicizing processing agents as a water-absorbing agent, there can be obtained a photocatalyst-containing fibre structure which can be used in sportswear applications and the like, where water absorption properties are required. When using an organic water-absorbing agent resin or hydrophilicizing agent, it is preferred that it be used within a range such that no decomposition, discoloration or malodour production occurs due to oxidation by the photocatalyst semiconductor.

It is also possible to add a coupling agent to the aforesaid binder, and in this way it is possible to enhance the adhesion between the inorganic and organic materials. In so-doing, chemical bonding forces mutually act between the fibre, binder and photocatalyst, with the result that the washing durability can be enhanced.

Next, by adding a coupling agent to the aforesaid binder, it is possible to enhance the adhesion between the inorganic and organic materials. In this way, chemical bonding forces mutually act between the fibre, binder and photocatalyst semiconductor and there is enhanced water durability.

The further addition of zeolite enhances the adsorption capacity in terms of odour components and raises the inorganic component content of the structure, and there is an effect in suppressing decomposition due to the photocatalyst. Moreover, it is possible to use zeolite on which there has been supported 0.01 to 5 wt % of a noble metal such as gold, platinum, silver, palladium or the like. In this way, the antibacterial effect is further enhanced.

Synthetic fibre or natural fibre can be used for the fibre structure of the present invention and there are no particular restrictions thereon, but it is preferred that the fibre structure be composed of fibre which contains at least 50 wt % polyester fibre. The polyester fibre here is preferably polyethylene terephthalate, polypropylene terephthalate, polybutylene terephthalate, polyhexamethylene terephthalate or the like. Again, the polyester from which the polyester fibre is composed may be polyester in which a third component has been copolymerized, and as preferred examples of such a third component employed in the copolymerization there are isophthalic acid, 5-sodiumsulphoisophthalic acid, methoxypolyoxyethylene glycol and the like. The functional characteristics of the present invention are displayed with outstanding effect in the case where the fibre structure is composed of at least 50 wt % polyester fibre, more preferably at least 70% and still more preferably 100%. Now, in the present invention, besides polyester fibre, there can be included synthetic fibre such as for example polyamide or polyacrylic, semi-synthetics such as acetate or rayon, or natural fibres such as wool, silk, cotton or flax.

The fibre structure referred to in the present invention encompasses not just fabric-form materials but also items composed of fibres like belt-form materials, string-form materials, yarn-form materials and the like. The structure and shape may be of any kind but a fabric-form chiefly comprising synthetic fibre is preferred, that is to say a woven material, knitted material or nonwoven material, and it may also be a composite material.

In the present invention, the polyester fibre may contain inert titanium oxide. As this inert titanium oxide there can be used for example the titanium oxide normally employed as a delustrant in the production of polyester synthetic fibre. By adding said inert titanium oxide, there may be a lessening of the effects, on the polyester fibre, of the redox action of the photocatalyst employed in the upper layer region. Said inert titanium oxide is normally added at the time of the polymerization of the polyester fibre, and from the point of view of spinnability and the yarn properties it is preferred that the average particle diameter be 0.1 to 0.7 $\mu$m and more preferably 0.2 to 0.4 $\mu$m.

Again, the amount of said inert titanium oxide added is preferably 0 to 5 wt %, and where required 0.5 to 4 wt %, in terms of fibre weight. If there is more than 5 wt %, the spinnability and the yarn properties are affected.

The cross-sectional aspect ratio of the polyester fibre in the present invention refers to a comparison of the outer circumferential length of fibre of non-circular cross-section to the outer circumferential length of circular cross-section fibre of the same cross-sectional area, or put another way, of the same denier, and specifically it denotes the value of the outer circumference of the fibre of non-circular cross-section divided by the outer circumference of the circular cross-section fibre. This invention may often be applied to fibre of circular cross-section but the greater the cross-sectional aspect ratio the greater the surface area per weight of fibre, and with it the greater the area of the photocatalyst layer, so that the effect thereof is proportionally increased. The cross-sectional aspect ratio of the fibre used will lie in the to range 1.2 to 2, and preferably 1.3 to 1.8. Where the value is greater than 2, there is the disadvantage that fibre production is difficult.

Next, an example of the method of producing the fibre structure of the present invention is explained.

Preferably with fine zeolite particles added to the binder, in particular zeolite on which 0.01 to 5 wt % of a noble metal such as gold is supported, and still more preferably with a coupling agent also added to the binder, there is mixed therewith an aqueous dispersion of a complex oxide of titanium and silicon, and this is used as the processing liquid.

Next, the fibre structure is immersed in this processing liquid, after which it is mangled and passed through a dry-cure stage. Alternatively, the processing liquid is prepared to a suitable viscosity, then applied by means of a knife coater or gravure coater or by printing, etc, after which it is dried and fixed at a temperature not exceeding 200° C.

In this way, it is possible to provide a fibre structure which as well as possessing satisfactory deodorant, antibacterial, antifungal and antisoiling properties of hitherto unattainable durability, also possesses outstanding functionality in terms of preventing residual/clinging odours.

EXAMPLES

Below, the present invention is explained in further detail by means of examples. In these examples the evaluation of the product quality was carried out by the following methods.

(Washing)

Using an automatic electric washing machine VH-3410 (made by the Toshiba Corp.), washing was carried out by strong agitation for 5 minutes at a bath ratio of 1:50, using 0.2% commercial detergent at 40±2° C., after which there was repeated two times the steps of water discharge and rinsing in flowing water for two minutes. This comprised one wash.

(Evaluation of Deodorant Properties by Means Detection Tube Method)

Ammonia gas was introduced into a 500 ml vessel containing 10 g of sample, to give an initial concentration of 200 ppm of ammonia and then the vessel was sealed and left for 1 hour, after which the residual ammonia concentration was measured with a gas detector tube. The percentage deodorizing was calculated based on the following relationship.

percentage deodorizing (%)=[1-(concentration measured by gas detector tube)/(initial concentration)]×100

By the same method, the residual gas concentration was measured in the case of 200 ppm of acetaldehyde after 1 hour, and in the case of 60 ppm of methyl mercaptan after 3 hours, and the percentage deodorizing of the gas calculated in each case.

(Olfactory Evaluation of Tobacco Odour Deodorant Property)

After inverting a 500 ml glass conical flask and leaving a smoke-producing lighted cigarette under the flask mouth for 5 seconds, the flask was quickly turned on its side, 3 g of sample introduced and the flask closed with a glass stopper. After leaving to stand for 1 hour, the stopper was removed and sensory evaluation of the remaining smell performed by 10 individuals. The odour at that time was evaluated on the following points basis, and mean values determined.

5: intense odour
4: strong odour
3: readily perceptible
2: weak odour perceptible
1: barely perceptible odour
0: no odour (Olfactory Evaluation of Residual-odour Prevention Property Based on Odour of isovaleric acid)

25 µl of a 0.01% aqueous isovaleric acid solution was measured out with a microsyringe and five 5 µl drops added to the central region of cloth which had been cut to size 10 cm×10 cm. With regard to the method of adding the drops, one drop was placed in the central region of the cloth and then four drops carefully added surrounding the central drop to make a pattern of five as on a dice. After leaving the cloth for 3 hours under a fluorescent light, sensory evaluation of the odour of the cloth was carried out by 10 individuals. The odour was evaluated on the same basis as the points evaluation in the case of the tobacco odour, and the mean determined.

(Degradation Odour)

A 10 cm×10 cm sample was spread out at the bottom of a 500 ml glass conical flask, and then this was closed with a glass stopper and left for 48 hours indoors at a west-facing glass window. Thereafter, the glass stopper was removed and sensory evaluation of the odour in the flask was carried out by 10 individuals. The odour was evaluated on the same basis as the points evaluation in the case of the tobacco odour, and the mean determined.

(Antibacterial Property Evaluation Method)

A standardized test method was employed as the evaluation method and a clinically isolated strain of *Staphylococcus aureus* was used as the test micro-organism. The test method comprised adding this test microorganism to sterilized test fabric, measuring the viable count after 18 hours of culturing, determining the number of organisms in terms of the increase in number of organisms, and then applying the following evaluation criterion.

On condition that log(B/A)>1.5, log (B/C) is taken as a measure of the difference in microbial propagation, and this should be at least 2.2.

Here, 'A' denotes the number of dispersed/recovered microorganisms directly after inoculation of the unprocessed item, 'B' denotes the number of dispersed/recovered microorganisms after culturing the unprocessed item for 18 hours, and 'C' denotes the number of dispersed/recovered microorganisms after culturing the processed item for 18 hours.

(Water Absorption Property)

The water absorption time was measured in accordance with Method A (dropwise method) in JIS L-1018. The smaller the value the better the water absorption.

(Method of Evaluating the Antisoiling Property)

Procedure 1 0.2 g of a soiling material of composition shown in Table 1, which had been dried for 2 hours at 100° C., a sample of length 10 cm and width 16 cm, and an ICI rubber pilling tube were together introduced into a polyethylene bag (20 litres). The bag was inflated with air at 20° C.×65%RH (to about 10 litres) and fastened with a rubber band.

TABLE 1

| Chemical Name | Weight % | Specification |
| --- | --- | --- |
| clay | 55.00 | Shiragaki clay pounded in mortar |
| Portland cement | 17.00 | JIS R5210 |
| silicon dioxide | 17.00 | JIS K8885 |
| ferric oxide | 0.50 | reagent CP grade |
| n-decane | 8.75 | reagent EP grade |
| carbon black | 1.75 | Tamagawa carbon black |

Procedure 2 The polyethylene bag from Procedure 1 was introduced into an ICI tester box and rotation carried out for 1 hour. Thereafter a sample was taken.

Procedure 3 The treated sample was washed once under the standard washing conditions. Procedures 1 to 3 were repeated a further two times.

Procedure 4 The L-values of the sample soiled and washed three times as described above, and of an untreated sample, were respectively measured using a colorimeter and the value of the difference ΔL calculated.

Example 1

A fibre fabric of weight per unit area 180 g/m² comprising 35wt % cotton and 65% polyester of single filament average fineness 3.3 dtex and circular cross-section, and which contained 0.35 wt % of inert titanium oxide of average particle diameter 0.3 μm, was subjected to scouring, drying, intermediate-setting and dyeing under the usual processing conditions.

Furthermore, as a photocatalyst, there was used a 20% aqueous dispersion of complex oxide of titanium and silicon of average primary particle diameter 7 nm and average specific surface area 150 m²/g. The average particle diameter at this time was 0.3 μm. Using this photocatalyst dispersion, an aqueous solution of processing liquid comprising the following components was employed in Example 1.

| | |
|---|---|
| titanium and silicon complex oxide (conc. 20%) (TR-T2, produced by the Daikyo Chemical Co.) | 1.0 wt % |
| alkyl silicate resin (conc. 20%) (CLG-520, produced by the Kyoeisha Chemical Co.) | 1.0 wt % |
| silicone resin (conc. 45%) (BY22-826, produced by Dow Corning Toray Silicone Co.) | 1.5 wt % |
| silane coupling agent (conc. 100%) (TSL-8350, produced by the Toshiba Silicone Co.) | 0.2 wt % |
| noble metal-supported type zeolite (conc. 20%) (Zeomic AW10N, produced by the Sinanen Zeomic Co.) | 0.3 wt % |

The aforesaid dyed fibre fabric was immersed in this processing liquid, then mangled to a pick-up of 80 wt % and dried for 2 minutes at 120° C., after which heat treatment was carried out for 1 minute at 180° C., and a structure containing photocatalyst at the fibre surface was obtained. Evaluation of the deodorant, antibacterial, antisoiling and water absorption properties, etc, of this fibre fabric was carried out. The results are shown in the table below.

Example 2

Processing Liquid 2 was produced by further adding 0.5 wt % of fluororesin (concentration 20%) [DIC Guard F-90, produced by Dainippon Ink & Chemicals] to the processing liquid in Example 1. Processing was carried out in the same way as in Example 1 using Processing Liquid 2 and a treated fabric with photocatalyst obtained. Evaluation of the deodorant, antibacterial, antisoiling and other properties of this fibre fabric was carried out. The results are shown in the table below.

Example 3

Processing Liquid 3 was produced by omitting the silane coupling agent in the processing liquid of Example 1. Processing was carried out in the same way as in Example 1 using Processing Liquid 3 and a treated fabric with photocatalyst obtained. Evaluation of the deodorant, antibacterial, antisoiling and other properties of this fibre fabric was carried out.

Example 4

Processing Liquid 4 was produced by omitting the silane coupling agent and the noble metal-supported zeolite in the processing liquid of Example 1. Processing was carried out in the same way as in Example 1 using Processing Liquid 4 and a treated fabric with photocatalyst obtained. Evaluation of the deodorant, antibacterial, antisoiling and other properties of this fibre fabric was carried out. The results are shown in the table below.

Example 5

Processing Liquid 5 was produced by adding 1.0 wt % of a hydrophilic polyester resin chiefly comprising polyalkylene glycol/polyester block copolymer (Nicepore PR-99, produced by the Nicca Chemical Co.) to the processing liquid of Example 1. Processing was carried out in the same way as in Example 1 using Processing Liquid 5 and a treated fabric with photocatalyst obtained. Evaluation of the deodorant, antibacterial, antisoiling, water absorption and other properties of this fibre fabric was carried out. The results are shown in the table below.

Example 6

5 wt % of sodium hydroxide NaOH was added to a 30 wt % solution of titanium tetrachloride $TiCl_4$, then the mixture left for a while, and titanium hydroxide $Ti(OH)_4$ obtained. This was treated with 25 wt % hydrogen peroxide and Processing Liquid 6 comprising non-crystalline titanium peroxide obtained. The dyed fibre fabric employed in Example 1 was immersed in Processing Liquid 6, then mangled to a pick-up of 80 wt % and dried for 2 minutes at 120° C., after which heat treating was carried out for 1 minute at 180° C., and there was obtained a fibre fabric with a non-crystalline titanium peroxide particle layer on the fibre surface. This fibre fabric was then processed with Processing Liquid 1 in the same way as in Example 1, and a treated fabric with photocatalyst obtained. Evaluation of the deodorant, antibacterial, antisoiling and other properties of this fibre fabric was carried out. The results are shown in the table below.

Example 7

By means of a PVD method, fine zeolite particles were affixed by vapour phase coating onto the dyed fibre fabric of Example 1. Subsequently, this fibre fabric was processed with the processing liquid of Example 1 in the same way as in Example 1, and a treated fabric with photocatalyst obtained. Evaluation of the deodorant, antibacterial, antisoiling and other properties of this fibre fabric was carried out. The results are shown in the table below.

Example 8

A processing liquid comprising

| | |
|---|---|
| alkyl silicate resin (conc. 20%) (MS51, produced by the Mitsubishi Chemical Corp.) | 20.5 wt % |
| methanol | 8.5 wt % |
| pure water | 70.0 wt % |
| sulphuric acid (conc. 20%) | 1.0 wt % | was employed as Processing Liquid 8. 5 g/m² (dry basis) of this Processing Liquid 8 was applied with a gravure roller onto the dyed fibre fabric surface of an artificial suede leather comprising a nonwoven material. Thereafter, processing of this fibre fabric surface was carried out with Processing Liquid 1 using a gravure roller in the same way, so that 7 g/m² was applied (dry basis) and a treated fabric with photocatalyst obtained. Evaluation of the deodorant, antibacterial, antisoiling and other properties of this fibre fabric was carried out. The results are shown in the table below.

Example 9

A fibre fabric of weight per unit area 180 g/m² comprising 35 wt % cotton and 65% polyester of single filament average fineness 3.3 dtex, having a flattened cross-shaped fibre section as shown in FIG. 1, and a cross-sectional aspect ratio of 1.5, and which contained 0.35 wt % of inert titanium oxide of mean particle diameter 0.3 μm, was subjected to scouring, drying, intermediate-setting and dyeing under the usual processing conditions.

This dyed fibre fabric was immersed in Processing Liquid 1, then mangled to a pick-up of 80 wt % and dried for 2 minutes at 120° C., after which heat treating was carried out for 1 minute at 180° C., and there was obtained a structure with photocatalyst on the fibre surface. Evaluation of the deodorant, antibacterial, antisoiling, water absorption and other properties of this fibre fabric was carried out. The results are shown in the table below.

Examples 10 to 15

Testing was carried out in the same way as in Example 1 except that the amounts of binder and complex oxide of titanium and silicon were varied. The results are shown in the table below.

Comparative Example 1

The dyed fabric in Example 1 was processed in the same way as in Example 1 using a processing liquid comprising the following components, and employing as the photocatalyst a 40% aqueous dispersion of a simple $TiO_2$ composition. The Results are shown in the table below. The average primary particle size of the photocatalyst was 20 nm and the average specific surface area was 50 m²/g.

| | |
|---|---|
| titanium oxide photocatalyst (conc. 40%) (STS-21, producedby Ishihara Sangyo Kaisha Ltd) | 0.5 wt % |
| alkyl silicate resin (conc. 20%) (CLG-520, produced by the Kyoeisha Chemical Co.) | 1.0 wt % |
| silicone resin (conc. 45%) (BY22-826, produced by Toray-Dow Corning Silicone Co.) | 1.5 wt % |
| silane coupling agent (conc. 100%) (TSL-8350, produced by the Toshiba Silicone Co.) | 0.2 wt % |
| noble metal-supported type zeolite (conc. 20%) (Zeomic AW10N, produced by Sinanen Zeomic) | 0.3 wt % |

The results obtained are shown in the table below.

Comparative Example 2

Example 1 was repeated, except that no photocatalyst was added to the processing liquid.

Tables 2 and 3 show the conditions and results for the various Examples and Comparative Examples. It will be clear from these tables that, when contrasted with the Comparative Examples, Examples 1 to 9 show a good balance of deodorant properties at an outstanding level. Furthermore, Examples 1, 2 and 5 are outstanding in their deodorant, antibacterial and antisoiling properties and in their durability. Of these, when Example 1 and Example 9 are compared, it can be seen that Example 1, which has the greater cross-sectional aspect ratio, has more outstanding deodorant, antibacterial and antisoiling properties, so the effect of the difference in cross-sectional aspect ratio is apparent. Moreover, it is clear that Example 5 is outstanding in its water absorption when compared to Example 1 and Comparative Example 1.

INDUSTRIAL APPLICABILITY

In accordance with the present invention, it is possible to offer a fibre structure possessing functional properties which can be widely utilized in, for example, clothing, and curtains, wall covering materials, sheet materials, bedding and other such interior materials, and the interior trim materials of automobiles and other vehicles.

TABLE 2

Composition of the Treatment Liquid
(weight percentage of effective component in the treatment liquid)

| | alkyl silicate resin | other silicone resin | fluororesin | zeolite | silane coupling agent | complex oxide of titanium and silicon | hydrophilic polyester resin | Notes |
|---|---|---|---|---|---|---|---|---|
| Example 1 | 0.2 | 0.68 | — | 0.06 | 0.2 | 0.2 | — | |
| Example 2 | 0.2 | 0.68 | 0.1 | 0.06 | 0.2 | 0.2 | — | |
| Example 3 | 0.2 | 0.68 | — | 0.06 | — | 0.2 | — | |
| Example 4 | 0.2 | 0.68 | — | — | — | 0.2 | — | |
| Example 5 | 0.2 | 0.68 | — | 0.06 | 0.2 | 0.2 | 0.2 | |
| Example 6 | 0.2 | 0.68 | — | 0.06 | 0.2 | 0.2 | — | titanium peroxide coated fibre |
| Example 7 | 0.2 | 0.68 | — | 0.06 | 0.2 | 0.2 | — | zeolite coated fibre |
| Example 8 | 0.2 | 0.68 | — | 0.06 | 0.2 | 0.2 | — | alkyl silicate coated fibre |
| Example 9 | 0.2 | 0.68 | — | 0.06 | 0.2 | 0.2 | — | polyester fibre with a cross-sectional aspect ratio = 1.5 used |
| Example 10 | 0.2 | 0.68 | — | 0.06 | 0.2 | 0.1 | — | |
| Example 11 | 0.2 | 0.68 | — | 0.06 | 0.2 | 1.0 | — | |

TABLE 2-continued

Composition of the Treatment Liquid
(weight percentage of effective component in the treatment liquid)

|  | alkyl silicate resin | other silicone resin | fluororesin | zeolite | silane coupling agent | complex oxide of titanium and silicon | hydrophilic polyester resin | Notes |
|---|---|---|---|---|---|---|---|---|
| Example 12 | 0.2 | 0.68 | — | 0.06 | — | 3.0 | — |  |
| Example 13 | 0.8 | — | — | — | — | 0.2 | — |  |
| Example 14 | — | 0.68 | — | — | — | 0.2 | — |  |
| Example 15 | — | — | 0.5 | — | — | 0.2 | — |  |
| Comp. Example 1 | 0.2 | 0.68 | — | 0.06 | 0.2 | — | — | 0.2 wt % of titanium oxide type photocatalyst added |
| Comp. Example 2 | 0.2 | 0.68 | — | 0.06 | 0.2 | — | — | no photocatalyst |

TABLE 3

|  | Deodorizing (%) | | | Tobacco Deodorizing (points) | | Isovaleric Acid Deodorizing (points) | | Antibacterial Property | | Water Absorption (secs) | Anti-Soiling Property | Degradation points |
|---|---|---|---|---|---|---|---|---|---|---|---|---|
|  | Odour A | Odour B | Odour C | Washing 0 times | Washing 10 times | Washing 0 times | Washing 10 times | Washing 0 times | Washing 10 times | Washing 0 times | ΔL Value | Washing 0 times |
| Example 1 | 100 | 98 | 93 | 2.2 | 2.7 | 0.5 | 1.0 | 5.9 | 5.8 | 180 | 7.7 | 1.9 |
| Example 2 | 100 | 97 | 92 | 2.4 | 2.6 | 0.5 | 1.2 | 5.3 | 5.0 | — | 5.1 | 2.1 |
| Example 3 | 100 | 96 | 91 | 2.4 | 3.8 | 0.6 | 3.4 | 5.2 | 4.3 | — | 17.1 | 2.1 |
| Example 4 | 100 | 95 | 90 | 2.7 | 3.8 | 0.7 | 3.4 | 4.4 | 3.0 | — | 16.8 | 2.0 |
| Example 5 | 98 | 98 | 90 | 2.4 | 2.6 | 0.5 | 1.0 | 5.6 | 5.3 | 0.5 | 8.3 | 2.3 |
| Example 6 | 96 | 97 | 89 | 2.5 | 3.7 | 0.6 | 3.6 | 5.4 | 3.1 | — | 16.1 | 1.7 |
| Example 7 | 98 | 95 | 90 | 2.8 | 3.5 | 0.6 | 3.5 | 5.3 | 3.1 | — | 16.4 | 1.6 |
| Example 8 | 97 | 93 | 90 | 2.7 | 3.7 | 0.6 | 3.6 | 5.5 | 3.3 | — | 16.9 | 1.8 |
| Example 9 | 100 | 99 | 93 | 2.1 | 2.5 | 0.5 | 1.0 | 6.1 | 5.9 | — | 7.5 | 2.2 |
| Example 10 | 95 | 93 | 91 | 3.3 | 4.0 | 2.0 | 4.0 | 3.1 | 2.3 | — | 18.0 | 1.0 |
| Example 11 | 98 | 98 | 98 | 2.0 | 2.2 | 0.1 | 1.0 | 6.5 | 6.2 | — | 6.3 | 3.5 |
| Example 12 | 100 | 100 | 100 | 2.0 | 2.3 | 0.1 | 0.8 | 7.5 | 7.3 | — | 6.8 | 4.0 |
| Example 13 | 98 | 97 | 91 | 2.2 | 3.9 | 0.5 | 1.9 | 4.3 | 3.0 | — | 8.9 | 2.0 |
| Example 14 | 99 | 98 | 92 | 2.1 | 3.2 | 0.5 | 1.2 | 4.4 | 3.9 | — | 8.5 | 2.0 |
| Example 15 | 100 | 99 | 93 | 2.4 | 3.8 | 0.6 | 2.8 | 4.5 | 3.1 | — | 4.8 | 2.5 |
| Comp. Ex. 1 | 78 | 75 | 78 | 4.3 | 4.5 | 3.5 | 4.0 | 2.4 | 2.9 | — | 19.8 | 5.0 |
| Comp. Ex. 2 | 60 | 43 | 35 | 4.5 | 4.8 | 4.8 | 4.8 | 3.1 | 2.0 | — | 19.9 | 1.0 |

Odour A = ammonia
Odour B = acetaldehyde
Odour C = methyl mercaptan

What is claimed is:

1. A fibre structure with deodorant or antimicrobial properties comprising: a fibre having on a surface thereof, a complex oxide comprising titanium and silicon, and a binder, wherein the complex oxide comprises 20–95 mol % of titanium oxide component and 5–80 mol % of silicon oxide component based on the total mol % of the complex oxide.

2. A fibre structure with deodorant or antimicrobial properties according to claim 1 wherein the binder comprises a resin selected from the group consisting of alkyl silicate resins, silicone resins and fluororesins.

3. A fibre structure with deodorant or antimicrobial properties according to claim 1, further comprising a zeolite on the fibre surface.

4. A fibre structure with deodorant or antimicrobial properties according to claim 1, further comprising a coupling agent on the fibre surface.

5. A fibre structure with deodorant or antimicrobial properties according to claim 1, further comprising a water-absorbing agent on the fibre surface.

6. A fibre structure with deodorant or antimicrobial properties which has on the fibre surface, as an intermediate layer, at least one layer selected from the group consisting of a titanium peroxide particle layer, a zeolite layer and an alkyl silicate layer, and which has a structure according to claim 1 as an upper layer region.

7. A fibre structure with deodorant or antimicrobial properties according to claim 1, wherein the complex oxide comprises fine particles of specific surface area 100–300 $m^2/g$.

8. A fibre structure with deodorant or antimicrobial properties according to claim 1, wherein the complex oxide comprises fine particles of average primary particle diameter in the range 1 to 20 nm.

9. A fibre structure with deodorant or antimicrobial properties according to claim 1, wherein the amount of complex oxide is 0.03 to 10 wt % in terms of the fibre structure.

10. A fibre structure with deodorant or antimicrobial properties according to claim 9, wherein the amount of complex oxide is 0.05 to 5 wt % in terms of the fibre structure.

11. A fibre structure with deodorant or antimicrobial properties according to claim 10, wherein the amount of complex oxide is 0.08 to 3 wt % in terms of the fibre structure.

12. A fibre structure with deodorant or antimicrobial properties according to claim 1, wherein the fibre contains at least 50 wt % polyester.

13. A fibre structure with deodorant or antimicrobial properties according to claim 12, wherein the polyester fibre contains 0.3 to 5 wt % of inert titanium oxide.

14. A fibre structure with deodorant or antimicrobial properties according to claim 12, wherein the polyester fibre has a cross-sectional aspect ratio of 1.2 to 2.

* * * * *

UNITED STATES PATENT AND TRADEMARK OFFICE
CERTIFICATE OF CORRECTION

PATENT NO. : 6,592,858 B1
DATED : July 15, 2003
INVENTOR(S) : Honda et al.

It is certified that error appears in the above-identified patent and that said Letters Patent is hereby corrected as shown below:

<u>Column 4,</u>
Line 13, please change "a silicon" to -- and silicon --.

<u>Column 5,</u>
Line 54, please delete "semiconductor";
Line 61, please delete the entire paragraph beginning with "Next, by adding".

Signed and Sealed this

Sixth Day of April, 2004

JON W. DUDAS
*Acting Director of the United States Patent and Trademark Office*